United States Patent [19]

Keeton

[11] Patent Number: 4,947,867

[45] Date of Patent: Aug. 14, 1990

[54] SURGICAL CLOTHING AND LABELING MEANS THEREFOR

[76] Inventor: William F. Keeton, 135 Woodchase Ct., Atlanta, Ga. 30319

[21] Appl. No.: 244,280

[22] Filed: Sep. 15, 1988

[51] Int. Cl.⁵ .............................................. A61F 13/00
[52] U.S. Cl. ...................................... 128/846; 40/586; 283/81; 283/75
[58] Field of Search ................ 128/896, 897, 849–856, 128/303 R, 155–157; 2/114, 244–246, DIG. 7; 40/1.5, 300, 633, 638–641, 586; 206/570, 438, 440; 283/74, 75, 81, 900

[56] References Cited

U.S. PATENT DOCUMENTS

| | | | |
|---|---|---|---|
| 3,693,618 | 9/1972 | Madden | 206/440 |
| 4,122,947 | 10/1978 | Falla | 206/569 |
| 4,314,415 | 2/1982 | De Woskin | 40/216 |
| 4,369,528 | 1/1983 | Vest et al. | 2/DIG. 7 |
| 4,375,133 | 3/1983 | Fenrich | 40/586 |
| 4,377,047 | 3/1983 | Adams, Jr. et al. | 40/586 |
| 4,530,349 | 7/1985 | Metzger | 128/897 |
| 4,564,977 | 3/1985 | King et al. | 2/DIG. 7 |
| 4,614,366 | 9/1986 | North et al. | 283/75 |
| 4,737,995 | 4/1988 | Wiley | 2/DIG. 7 |
| 4,739,761 | 4/1988 | Grandon | 128/303 R |

Primary Examiner—Randall L. Green
Assistant Examiner—K. M. Reichle
Attorney, Agent, or Firm—James B. Middleton

[57] ABSTRACT

A system for protection of a patient entering surgery includes both a heat retaining gown and labels for assuring that the proper patient receives the proper surgery. The gown is made of a disposable material so that the gown as a whole can remain in place on the patient, while portions thereof are cut away to allow required access to the body. Openings can be provided in advance for usual procedures such as blood pressure monitoring. The labels can be placed either on the gown, or on the patient. One label can provide information as to patient and surgeon names, procedure and the like, and another label can include arrows to point to the proper site. If desired, the two labels can be combined.

9 Claims, 1 Drawing Sheet

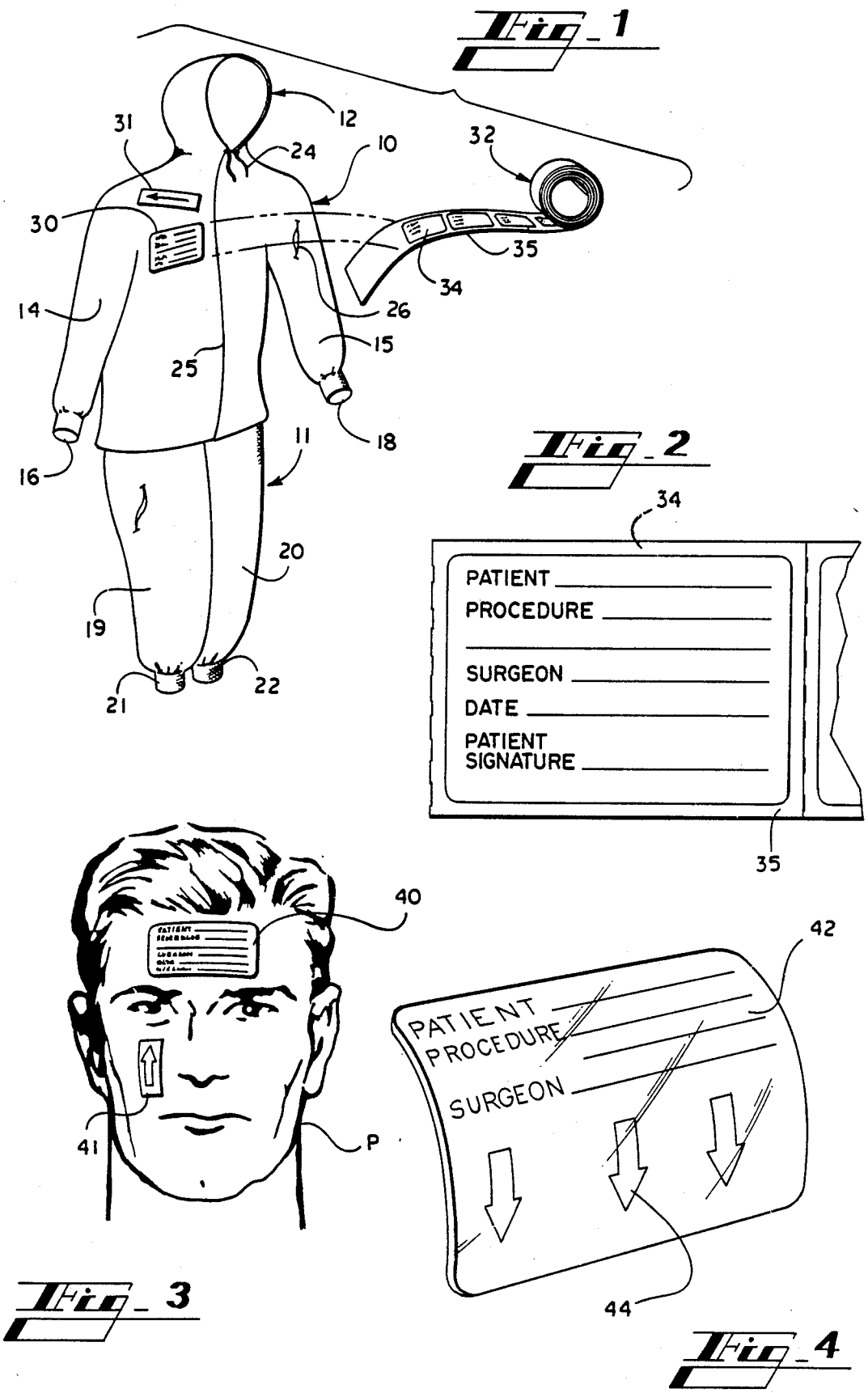

SURGICAL CLOTHING AND LABELING MEANS THEREFOR'

INFORMATION DISCLOSURE STATEMENT

When a patient is to undergo surgery, the patient is customarily dressed in a surgical robe or gown. These surgical robes or gowns are necessarily easy to put on and to take off, and are generally openable throughout their complete length. While such gowns may have some form of fastening means, the gowns are generally not adequately closable for complete comfort of the patient.

When a patient is in the operating room, and the patient is wearing a surgical gown, either the garment is opened full length so the patient is totally exposed, or a large, readily removable portion is removed, again exposing a very large portion of the patient's body.

The prior art surgical gowns are undesirable from the patient's standpoint for reasons of both comfort and modesty. The gowns tend to be designed more for purposes of examination and ease of putting on and taking off, and are not designed for patient comfort. Also, the gowns tend to expose large portions of the patient's body: if not always, then inadvertently due to the openness of the gown. Additionally, the prior art garments are undesirable in the operating room because of the lack of protection to the patient. Operating rooms are generally maintained at rather low temperature, so the extensive exposure of the patient's body causes the patient to lose body heat. It will also be understood that anesthetics tend to cause vasodilation which naturally leads to additional heat loss and when the body cavity is open the tendency towards heat loss, is increased. At the same time it will be understood that the usual bodily reaction of shivering to generate heat and regain the proper body temperature is not possible under general anesthesia.

In addition to the other, rather general, problems involved, if the body temperature of the patient falls below about 34° C. (approximately 93° F.) an overdose of anesthesia can easily occur. At this temperature the concentration of the anesthesia tends to be considerably reduced to maintain the proper level. Also, once a patient's body cools to this extent it is difficult to regain the proper body temperature.

If a patient's body is allowed to cool too much while in the operating room, when the anesthesia wears off the patient tends to use the shivering mechanism automatically in an effort to regain the heat. Shivering causes an increase in oxygen consumption with the resulting circulatory stress. Those skilled in the art will understand that this temperature loss in the very old, the very young, the ill or the cachectic is especially dangerous and should be guarded against.

The prior art efforts to solve these problems have included efforts to cover parts of the patient's body with sheets or the like, but these tend to be loose, and fail to maintain sufficient heat. Body extremities have been wrapped in various materials, including plastic sheeting, but these procedures are difficult to handle effectively, and result in undesirable bulk in the operating room. Another technique is to place the patient on a blanket that produces heat for the patient. One of the primary difficulties with this heating blanket is that the blanket is generally flat so that only a few portions of the patient's body actually contact the blanket to absorb the heat. Even when a patient is reclining on the back or front, a relatively small percentage of the body contacts the blanket; and, patients in other positions may have even less contact with the blanket. In extreme cases, as with some orthopedic tables and the like, almost none of the body would contact the blanket so that a warming blanket would be totally useless.

Regardless of the form of covering, it will be understood that coverings generally are relatively non-personal so that all patients look pretty much alike when under a surgical drape, or in various surgical gowns and the like. Thus, there is a need for means for covering a patient to maintain sufficient body heat, and to identify the patient and the proposed surgical procedure adequately to prevent mistakes.

SUMMARY OF THE INVENTION

This invention relates generally to surgical garb, and is more particularly concerned with disposable, heat retaining garb, and labelling means for use in conjunction therewith.

The present invention provides surgical garb designed for substantially covering the entire body of a patient. It is contemplated that the garment will include openings for attachment of the usual material to the patient, such as a blood pressure cuff or the like. Additionally, the garment is preferably made of an inexpensive material, such as a nonwoven fabric, that can be easily cut away to expose only the required portion of the patient's body. Furthermore, it is contemplated that labeling means will be used on the patient to designate the area for the intended surgery. The labelling means may take the form of a single label for recording required information, along with arrows or other directing means to indicate the specific location of the surgery. Alternatively, a plurality of labels may be utilized so that one or more labels will provide written information, and additional labels may indicate directions and/or locations.

The present invention therefore provides a highly effective system both to maintain a patient in comfort, and to place information directly on the patient to convey information about the particular procedure proposed for the patient.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing a complete surgical garment having a plurality of labels thereon, and showing additional labeling means in conjunction therewith;

FIG. 2 is an enlarged plan view showing one form of label for use in conjunction with the present invention;

FIG. 3 is a fragmentary view showing another use of a plurality of labels on a patient; and, FIG. 4 is a perspective view showing a slightly different form of label substantially of the type shown in FIG. 3.

DETAILED DESCRIPTION OF THE EMBODIMENTS

Referring now more particularly to the drawings, and to those embodiments of the invention here presented by way of illustration, FIG. 1 illustrates the surgical garment made in accordance with the present invention, and having labelling means thereon.

Those skilled in the art will understand that any of numerous materials may be utilized for the surgical garment made in accordance with the present invention. The material must be sufficiently inexpensive to allow the entire device to be disposable, but this includes numerous plastic sheet materials, a number of paper materials, and several inexpensive nonwoven fabrics. The nonwoven fabrics are frequently used for disposable surgical drapes, surgeons' gowns and the like, and such fabrics are readily available in several different weights, with and without a plastic substrate or lining. It is contemplated that any of these materials may be used, depending on the particular features desired. The device may be made in both heavy-weight and light-weight, and of course may be made in several different sizes to cover a wide range of patients.

Looking at FIG. 1 in more detail, it will be seen that the garment includes a shirt generally designated at 10, pants generally designated at 11, and a hood generally designated at 12. The shirt 10 includes sleeves 14 and 15 having cuffs 16 and 18. Again, those skilled in the art will realize that inexpensive, knit cuffs are readily available for use on the sleeves 14 and 15 to assist in retaining the patient's body heat.

The pants 11 similarly include leg portions 19 and 20, the leg portions 19 and 20 including cuffs 21 and 22, the cuffs 21 and 22 preferably being formed of generally elastic, knit material for assisting in retaining body heat.

The hood 12 includes generally a head covering; and, while the hood 12 is here illustrated as formed integrally with, or attached to, the shirt 10, it will also be readily understood that the hood 12 can be separately formed and attached by adhesive means or the like. It will also be seen that, for better control in the vicinity of the face of the patient, the hood 12 is provided with drawstrings 24.

Those skilled in the art will understand that man fastening means are available, and pressure sensitive adhesive means are well known in the art and are well adapted to simple closure of inexpensive fabrics. Thus, the shirt 10 may be open along the line 25, and closable by adhesive means or the like. Though not here illustrated, the pants 11 may utilize knit material such as the cuffs 16 or 18 at the waist, or may utilize a drawstring 24 at the waist to hold the pants on a patient.

It is contemplated that the surgical garment will include certain relatively standard openings such as the opening 26 for placement of the blood pressure cuff. Additional openings, as for catheters and the like may also be provided; however, it is an important feature of the present invention that the material of the surgical garment is easily cuttable by the operating room staff so that additional openings can be made whereever desired in the surgical garment. Thus, whether the procedure is extremely common, or extremely rare, appropriate openings can be provided for needles, catheters, various sensors and the like.

Another important feature of the present invention is the use of labelling means. In FIG. 1 it will be seen that there is a label indicated at 30, the label 30 including written material which may comprise the patient's name, the surgeon's name, the surgical procedure intended for the patient and the like. In addition to the label 30, there is a label 31 which constitutes directing means. In the case of the label 31 in FIG. 1 of the drawings, it will be seen that the label 31 is an arrow pointing to the right shoulder of the patient. By way of example, if the label 30 indicates that the patient is to undergo an operation on the shoulder, the label 31 assists in directing attention to the proper shoulder. With this combination, it will be understood that the surgical garment can be cut away to expose the shoulder, even while leaving the labeling means 30 and 31 in position so that the information remains with the patient in the operating room.

It will also be seen in FIG. 1 that there is a roll of labels indicated at 32. While labels may be provided in any convenient form, the roll 32 is one example wherein a plurality of pressure sensitive labels 34 is carried by a backing 35. Thus, one or a plurality of labels 34 can be removed from the backing 35 and appropriately attached to the patient and/or to the surgical garment.

Looking now at FIG. 2 of the drawings, one form of label is shown. By way of example, the label shown in FIG. 2 includes a blank for the patient's name, for the procedure proposed for the patient, the name of the surgeon to perform the operation, the date of the operation and the patient's signature. Through use of such a label, the patient is identified, the surgeon is identified, and the procedure to be used is stated. The date of the operation can be included, and the patient's signature can be included to indicate his consent. Such a label can be filled out before the patient leaves his hospital room or is otherwise prepared for surgery. The label can be filled out, signed by the patient, and affixed to the patient while the patient is fully aware, thereby assisting in preventing any errors.

Looking at FIG. 3 of the drawings, it will be seen that a label such as that shown in FIG. 2 of the drawings might be affixed directly to the skin of the patient. As is shown in FIG. 3, there is a label designated at 40 affixed to the forehead of the patient P. Here it is contemplated that the patient is scheduled for some form of eye surgery, and there is an additional label 41 constituting directing means for directing attention to the right eye of the patient. With such an arrangement, it will be understood that, even in the operating room itself, the patient himself is appropriately labelled so there will be no oversight during preparation of the patient for actual surgery.

A modification of the arrangement in FIG. 3 is shown in FIG. 4. In some instances, the label carrying the written information may also carry the directing means. For example, if a patient's knee is to be operated on, a label such as that shown in FIG. 4 can be filled out and placed on the patient's thigh adjacent to the appropriate knee. The written material at 42 would carry the general information required, and the directing means indicated at 44 would point precisely to the site of operation.

It will therefore be understood that the present invention provides a system for surgery wherein the patient is protected by being well covered to retain body heat, and the patient is appropriately labelled to be sure the proper patient receives the proposed surgical procedure, and in the right location. For labels such as the labels 34, it will be understood that almost any label could be utilized to stick to the surgical garment. Preferably one would use a generally opaque background so that writing on the label would show clearly. As indicated at FIG. 1, the labels can be provided on rolls such as the roll 32, and any number of labels can be utilized for complete labeling of the patient, the procedure etc.

When a label is to be placed directly on the patient, one would generally label the patient after the patient has been prescrubed for surgery.- Because the patient will be relatively sterile, one would of course use a sterile label on the patient. Those skilled in the art will devise many forms of specific labels, but one product that is usable for such labelling is the transparent surgical dressing manufactured by 3M, Medical-surgical Division under the trademark TEGADERM. This device includes a sealed dressing that is completely sterile and is intended for use on a patient. Nevertheless, various pens will write on the material so that the dressing can be used as a label in accordance with the present invention. It will also be understood, of course, that such material can be preprinted substantially as shown in FIG. 2 of the drawings in order to designate the information to be supplied.

In view of the foregoing discussion, it will be understood that the forehead label 40 might be used for all patients. With the garment as illustrated in FIG. 1, it will be noted that the patient's forehead will always be visible; therefore, one could place a forehead label on each patient to provide a general identification of the patient, procedure, surgeon etc. One can then provide additional labels as appropriate on the body of the patient, and/or on the surgical garment to point to the particular location for the surgery, and perhaps provide some additional factual information about the surgery.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

What is claimed:

1. Patient protection apparatus, for use in protecting a patient scheduled for surgery, comprising a disposable surgical gown, said gown including a shirt having at least one opening therein for allowing access to the body of the patient, said gown being formed of a disposable material and easily cuttable for providing access to the body of the patient through said gown, and labelling means receivable selectively on said gown and the patient for identifying the patient and located for providing additional information about the location of the surgery.

2. Patient protection apparatus as claimed in claim 1, said labelling means including directing means for pointing to the proposed area of surgery on the patient.

3. Patient protection apparatus as claimed in claim 2, said labelling means including a first label, said first label including information for identifying the patient, the surgeon and the proposed surgical procedure, and a second label including at least one arrow adapted to be pointed to the proposed surgical site.

4. Patient protection apparatus as claimed in claim 2, said labelling means including transparent labels adapted to be selectively received on the skin of the patient, said transparent labels being sterile.

5. Patient protection apparatus as claimed in claim 4, said first label adapted to be received on the forehead of the patient for constant visibility thereof.

6. A system for protection of a patient preparing for surgery, said system including labelling means receivable on the patient for identifying the patient and the proposed surgical procedure for the patient, said labelling means including directing means for pointing to the proposed site of surgery.

7. A system for protection of a patient as claimed in claim 6, said labelling means including a first label carrying information for identifying the patient, and a second label carrying said directing means.

8. A system for protection of a patient as claimed in claim 7, said system further including a surgical gown for retaining the patient's body heat, at least one of said labels being received on said gown.

9. A system for protection of a patient as claimed in claim 8, said gown being formed of disposable material and easily cuttable for allowing access through said gown to the proposed surgical site while retaining said labelling means on the patient.

* * * * *